(12) United States Patent
Walker

(10) Patent No.: US 11,093,688 B2
(45) Date of Patent: Aug. 17, 2021

(54) ENHANCING READING ACCURACY, EFFICIENCY AND RETENTION

(71) Applicant: Mayo Foundation for Medical Education and Research, Rochester, MN (US)

(72) Inventor: Randall C. Walker, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 16/717,514

(22) Filed: Dec. 17, 2019

(65) Prior Publication Data

US 2020/0125791 A1 Apr. 23, 2020

Related U.S. Application Data

(62) Division of application No. 15/306,190, filed as application No. PCT/US2015/026430 on Apr. 17, 2015, now Pat. No. 10,515,138.

(Continued)

(51) Int. Cl.
*G06F 40/106* (2020.01)
*G16H 10/60* (2018.01)
(Continued)

(52) U.S. Cl.
CPC .......... *G06F 40/106* (2020.01); *G06F 40/103* (2020.01); *G06F 40/117* (2020.01);
(Continued)

(58) Field of Classification Search
None
See application file for complete search history.

(56) References Cited

U.S. PATENT DOCUMENTS 4,661,924 A 4/1987 Okamoto et al.
4,864,502 A 9/1989 Kucera et al.
(Continued)

FOREIGN PATENT DOCUMENTS

EP 0327266 8/1995
WO WO 1998/06082 2/1998
(Continued)

OTHER PUBLICATIONS

"To Read or Not to Read: A Question of National Consequence," National Endowment for the Arts., Research Report #47, Nov. 2007, Retrieved Sep. 7, 2017, Retrieved from URL: https://www.arts.gov/sites/default/files/ToRead.pdf, 98 pages.

(Continued)

*Primary Examiner* — Howard Cortes
(74) *Attorney, Agent, or Firm* — Fish & Richardson P.C.

(57) ABSTRACT

This document provides systems and methods for altering text presentation to increase reading accuracy, efficiency, and retention. This can include identification text specific attributes from machine readable text (through parsing of the text), varying the text presentation in accordance with the attributes, and creating an enhanced visual product for enhancing the reading experience. For example, a computer system can extract attributes such as parts of speech from an input sentence and display that sentence in cascading text segments down and across a display screen. The system can further use domain-specific dictionaries derived from domain-specific texts to identify domain-specific compound noun phrases and verb phrases that require specific linguistic tagging to be usable in other linguistic analysis steps.

20 Claims, 6 Drawing Sheets

Related U.S. Application Data

(60) Provisional application No. 61/984,270, filed on Apr. 25, 2014.

(51) Int. Cl.
| | |
|---|---|
| *G06F 40/30* | (2020.01) |
| *G06F 40/103* | (2020.01) |
| *G06F 40/117* | (2020.01) |
| *G06F 40/211* | (2020.01) |
| *G06F 40/253* | (2020.01) |
| *G06F 40/289* | (2020.01) |

(52) U.S. Cl.
CPC .......... *G06F 40/211* (2020.01); *G06F 40/253* (2020.01); *G06F 40/289* (2020.01); *G06F 40/30* (2020.01); *G16H 10/60* (2018.01)

(56) References Cited

U.S. PATENT DOCUMENTS

| | | |
|---|---|---|
| 4,887,212 A | 12/1989 | Zamora et al. |
| 5,060,155 A | 10/1991 | van Zuijlen |
| 5,068,789 A | 12/1991 | van Vliembergen |
| 5,083,268 A | 1/1992 | Hemphill et al. |
| 5,146,405 A | 9/1992 | Church |
| 5,297,040 A | 3/1994 | Hu |
| 5,708,822 A | 1/1998 | Wical |
| 5,721,938 A | 2/1998 | Stuckey |
| 5,802,533 A | 9/1998 | Walker |
| 5,878,385 A | 3/1999 | Bralich et al. |
| 5,926,784 A | 7/1999 | Richardson et al. |
| 5,930,746 A | 7/1999 | Ting |
| 5,960,384 A | 9/1999 | Brash |
| 6,108,620 A | 8/2000 | Richardson et al. |
| 6,182,028 B1 | 1/2001 | Friedman |
| 6,182,029 B1 | 1/2001 | Friedman |
| 6,236,959 B1 | 5/2001 | Weise |
| 6,275,791 B1 | 8/2001 | Weise |
| 6,279,017 B1 | 8/2001 | Walker |
| 7,036,075 B2 | 4/2006 | Walker |
| 7,136,806 B2 | 11/2006 | Miyahira et al. |
| 7,184,950 B2 | 2/2007 | Weise |
| 7,233,891 B2 | 6/2007 | Bond et al. |
| 7,562,008 B2 | 7/2009 | Chan |
| 7,765,471 B2 | 7/2010 | Walker |
| 8,209,601 B2 | 6/2012 | Bever et al. |
| 8,612,204 B1 | 12/2013 | Uszkoreit et al. |
| 9,390,087 B1 | 7/2016 | Roux |
| 9,836,451 B2 | 12/2017 | Halbani |
| 2004/0253568 A1 | 12/2004 | Shaver-Troup |
| 2005/0108001 A1* | 5/2005 | Aarskog .............. G06F 40/289 704/10 |
| 2006/0235881 A1* | 10/2006 | Masarie ................. G16H 20/10 |
| 2007/0179776 A1 | 8/2007 | Segond |
| 2009/0070103 A1* | 3/2009 | Beggelman ............. G06F 40/20 704/9 |
| 2010/0114628 A1* | 5/2010 | Adler ................... G06Q 10/063 705/7.11 |
| 2010/0250235 A1* | 9/2010 | Madan .................. G06F 40/242 704/9 |
| 2010/0257444 A1* | 10/2010 | Bever ................... G06F 40/106 715/256 |
| 2011/0195384 A1 | 8/2011 | Palacios |
| 2012/0303356 A1* | 11/2012 | Boyle ..................... G06F 40/30 704/9 |
| 2013/0238313 A1* | 9/2013 | Alshinnawi ........... G06F 40/247 704/9 |
| 2014/0142924 A1 | 5/2014 | Friedman |
| 2015/0088484 A1* | 3/2015 | Bostick .................. G06F 40/40 704/2 |
| 2015/0106157 A1* | 4/2015 | Chang ................ G06Q 30/0201 705/7.29 |
| 2015/0186504 A1 | 7/2015 | Gorman |
| 2017/0011119 A1 | 1/2017 | Ghannam |
| 2017/0046311 A1 | 2/2017 | Walker |

FOREIGN PATENT DOCUMENTS

| | | |
|---|---|---|
| WO | WO 1999/39255 | 8/1999 |
| WO | WO 2010/105216 | 9/2010 |

OTHER PUBLICATIONS

Bever et al., "Spacing printed text to isolate major phrases improves readability," Visible Language., 25:75-87, 1990.

Dornescu et al., "A tagging approach to identify complex constituents for text simplification," Proceedings of recent advances in Natural Language Processing., 221-229, Sep. 7, 2013.

European Search Report in International Application No. EP 15782950.8, dated Nov. 22, 2017, 14 pages.

Extended European Search Report in International Application No. EP15782950.8, dated Feb. 28, 2018, 17 pages.

Gulbrandsen et al., "Paper or Screen, Mother Tongue or English: Which is Better? A Randomised Controlled Trial," JAMA., 287(21), 2851-2853, Jun. 5, 2002.

Hindle and Rooth., "Structural ambiguity and lexical relations," Computational Linguistics., 19:103-120, 1993.

International Preliminary Report on Patentability in International Application No. PCT/US2015/026430, dated Nov. 3, 2016, 9 pages.

International Search Report and Written Opinion in the International Application No. PCT/US2015/026430, dated Sep. 8, 2015, 12 pages.

Invitation to Pay Additional Fees in International Application No. PCT/US2015/026430, dated Jun. 25, 2015, 2 pages.

Knuth and Plass., "Breaking Paragraphs into Lines," Software-Practice and Experience., 11(11):1119-1184, Nov. 1981.

Kubon et al., "Segmentation of complex sentences," Text, Speech and Dialogue Lecture Notes in Artificial Intelligence., 151-158, Jan. 1, 2006.

Pilcher et al., "Language performance under sustained work and sleep deprivation conditions," Aviat Space Environ Med., 78(5 Suppl):B25-B38, May 2007.

Roberts et al., "Effects of Peer Review and Editing on the Readability of Articles Published in Annals of Internal Medicine," JAMA., 272:119-121, Jul. 13, 1994.

Schneps et al., "History of Reading Struggles Linked to Enhanced Learning in Low Spatial Frequency Scenes," PLOS ONE., 7(4):e35724, 2012, 13 pages.

\* cited by examiner

"Normally we do this
　　as an outpatient,
　but
　　in her case,
　　　because of her general debility,
　I would do
　　her
　　　as an inpatient
　　and then we would
　　　　more than likely try
　　　　　to see
　　　　　　if we
　　　　　　　can make
　　　　　　　　arrangements
　　　　　　　　　for a perhaps
　　　　　　　　　　one to two week stay
　　　　　　　　　　　in an extended-care facility
　　just because
　　　she is limited
　　　with her mobilities
　　　　and transfers
　　　　　and wound care abilities."

FIG. 3A

"Normally
  we do this as an outpatient,
 but in her case,
    because of her general debility,
 I would do her as an inpatient
    and then we would more than likely try
     to see if we can make arrangements
       for a perhaps one to two week stay
        in an extended-care facility
    just because she
     is limited with her mobilities
      and transfers and wound care abilities."

FIG. 3B

ENHANCING READING ACCURACY, EFFICIENCY AND RETENTION

CROSS REFERENCE TO RELATED APPLICATIONS

This application is a divisional of U.S. application Ser. No. 15/306,190, filed Oct. 24, 2016, which is a National Stage Application under 35 U.S.C. § 371 that claims the benefit of Application Serial No. PCT/US2015/026430, filed Apr. 17, 2015, which claim the benefit of U.S. Provisional Ser. No. 61/984,270 filed Apr. 25, 2014. This disclosures of the prior applications are considered part of (and are incorporated by reference in) the disclosure of this application.

BACKGROUND

1. Technical Field

This document relates to systems and methods for improving reading accuracy, efficiency, and retention, particularly for readers of complex, technical, or specialized text.

2. Background Information

A large part of the communication and information in health care, including the exchange between patients and physicians, and among physicians collaborating in the care of a patient, is encoded in natural spoken language in text form (e.g., English).

Health care professionals, through their education, exhibit good reading performance in general. However, once professionals graduate from formal education settings, there are few reasons or opportunities to assess one's accuracy or efficiency in reading such medical texts.

Moreover, the systematic use of such medical texts in the delivery of health care services, including contexts that constrain time allowed for reading the texts, assumes that reading performance among the individuals using the texts is already standardized, and reasonably homogenous across the working group and over the entire spectrum of health care delivery circumstances and time segments.

Variations in reading performance, in speed and/or accuracy, can lead to unexpected variations in health care outcomes—through delays, misinterpretation, or incomplete understanding of medical text content.

SUMMARY

This document provides systems and methods for altering text presentation to increase reading accuracy, efficiency, and retention. This can include identification of text specific attributes from machine readable text (through parsing of the text), varying the text presentation in accordance with the attributes, and creating an enhanced visual product for enhancing the reading experience. For example, a computer system can extract attributes such as parts of speech from an input sentence and display that sentence in cascading text segments down and across a display screen. The segmentation and horizontal displacement is determined by applying rules which utilize parts of speech, punctuation, and reader-preferences. The color of the text and background can also be varied depending on the parts of speech and on the position of sentences within paragraphs and paragraphs within chapters. The system can further use domain-specific dictionaries derived from domain-specific texts to identify domain-specific compound noun phrases and verb phrases that require specific linguistic tagging to be usable in other linguistic analysis steps. Sources of domain-specific texts can include medical texts such as electronic medical records, medical dictionaries, medical text books, medical trade publications, and the like. Other examples of domain-specific areas of text that can be included for use in creating a domain-specific dictionary of multiple-word phrases include legal texts, scientific texts, accounting texts, engineering texts, or texts for any other specialized area that often includes specific terminology.

The system can also be used to assess a difficulty level for one or more medical texts, and to track reading performance for one or more readers of the medical texts. The difficulty level and/or tracked reading performance information can be compared to tracked patient outcomes for patients associated with the medical texts. This comparison can be used to identify one or more optimal complexity levels for medical texts. The identified optimal complexity levels can be used to modify future presentations of the medical texts, or to assist in development of similar medical texts in the future.

Various advantages of the system and methods for improving reading accuracy, efficiency, and retention include the following. The systems and methods can allow for more efficient time usage of highly specialized professionals such as doctors, other medical professionals, lawyers, engineers. Additionally, medical outcomes for patients can be improved. Furthermore, complex texts regarding patient care and treatment can be quickly read and understood to allow for the best possible patient treatment.

DESCRIPTION OF THE DRAWINGS

FIG. 1 is a display screen for an electronic medical record that includes text in an original form.

FIG. 2 is a display screen for the electronic medical record of FIG. 1 that includes a varied presentation for the text.

FIGS. 3A-3B show a sample text that has been enhanced using two different reader specific enhancement processes.

DETAILED DESCRIPTION

Figure 4:
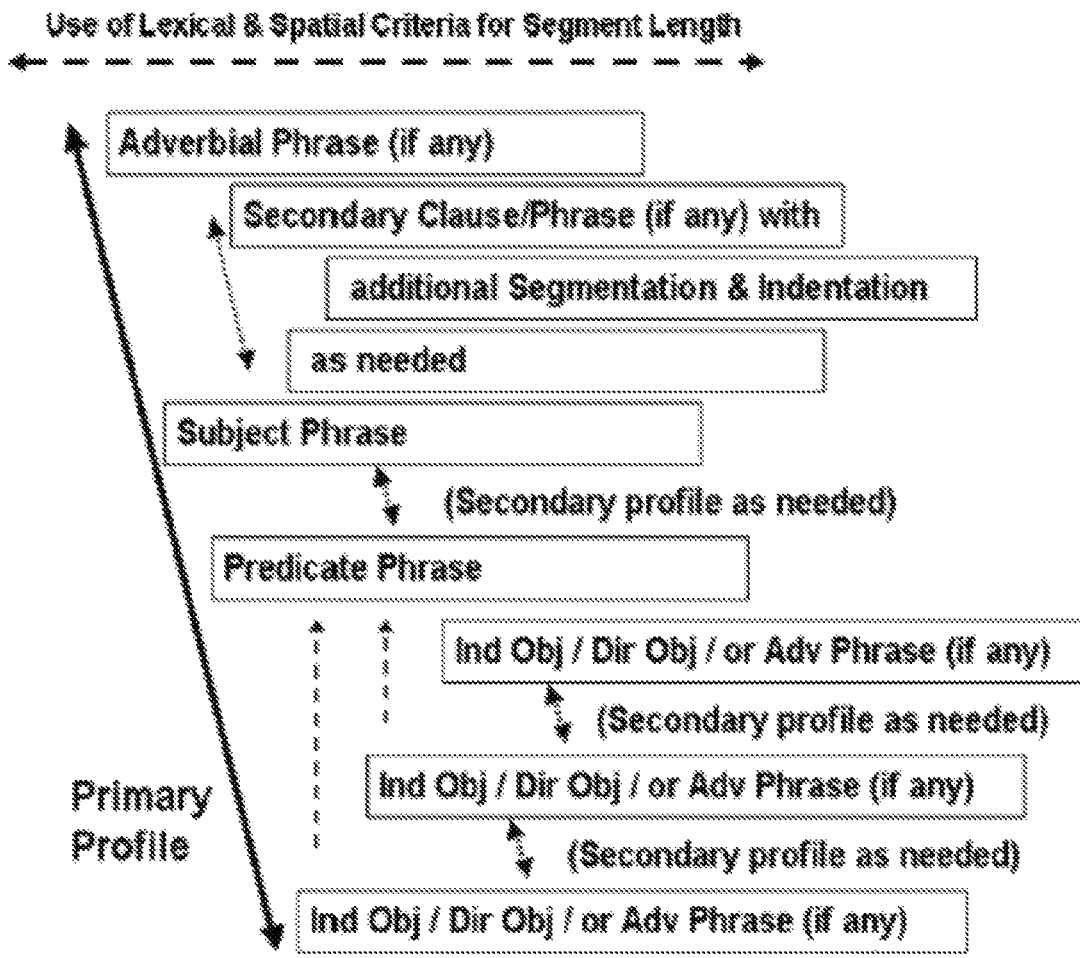
FIG. 4 shows a flow for a process for identifying specific attributes for a text.

This document provides systems and methods for altering text presentation to increase reading accuracy, efficiency, and retention. This can include parsing domain-specific texts to identify terms (both individual words, and multiple-word phrases) that are specific to a specified subject matter, more frequently used in association with the specified subject matter, or have one or more different meanings or associated parts-of-speech when used in the context of the specified subject matter. For example, a medical language database enrichment process can include parsing through large corpora of clinical texts to identify domain-specific compound noun phrases and compound verb phrases, or other multiple-word phrases that require specific linguistic tagging in association with medical texts (such as electronic medical records) to be usable in other linguistic analysis steps.

A system or apparatus practicing the below described methods can modify text presentation through the use of responsive, multidimensional attributive typesetting, entailing: extracting attributes from a machine-readable text; enriching the text with tags based on the extracted attributes;

enhancing the presentation of the text using the tags that had been placed into the enriched text; further enriching the text with user-based interaction data tags with the enhanced text, dynamically combining user-interaction tag data with attribute enrichment tags to create enlivened text that responds to users' inputs with sentence-specific responses.

The enrichment process can include identifying, through repeated occurrences, high-probability noun- and verb-phrases, while using contingency tags that will verify, within specific contexts, whether the compound phrase function should be kept or over-ruled. For example, a computer system can access one or more texts that are related to a specialized subject matter. Specialized subject matters could include, for example, medicine, law, engineering, biology, physics, philosophy, civics, or any other specialized area having its own specialized terminology. The system can then parse those texts to identify multiple-word phrases that are repeated throughout the texts and identify the repeated phrases as being potential domain-specific phrases. In some implementations, identifying domain-specific phrases can include identifying multiple-word phrases (i.e., specific word combinations) that appear in one or more texts more than a threshold number of times.

For example, the system can be used to parse a specialized text that is identified as a medical text (e.g., an Electronic Medical Record (EMR)). The medical text can include the sentence "Elective hip surgery in a patient with congestive heart failure is not an option that the medical team would consider." The system can identify the multiple word phrase "congestive heart failure" as a phrase that should be treated as a single term. As another example, when parsing a non-medical text containing the sentence "The Apollo 13 engineer believed in his heart failure is not an option," the system can identify that the phrase "heart failure" in this non-medical context should not be treated as a single term, but as two individual terms "heart" and "failure."

The system can then identify one or more definitions and one or more parts-of-speech for each identified domain-specific phrase. This can include inferring definitions and parts-of-speech through analysis of the texts from which the domain-specific phrases are drawn, or accessing domain-specific dictionaries or other resources that include specified definitions for the domain-specific phrases. In some implementations, it is only necessary for the system to identify one or more parts-of-speech for the identified domain-specific phrases and the system does not determine definitions for the identified domain-specific phrases.

Returning to the above example, when the phrase "congestive heart failure" is found in the specialized medical text, the system can identify the part-of-speech for the term as "noun." By contrast, in the non-medical text, the individual terms "heart" and "failure" can be identified as separate terms, each having a part-of-speech of "noun."

The medical language database enrichment process can also include identifying potential domain-specific phrases that should ultimately not be treated as a single term, but rather each word should be treated as an individual term. For example, a first parsing process for a set of text can identify a first set of potential domain-specific multiple-word phrases. The system can then perform a process that attempts to identify domain-specific definitions and parts-of-speech for each of the identified phrases. Some of the phrases identified as potential domain-specific phrases may not have definitions or parts-of-speech that are specific to a particular specialization area (e.g., medicine, law, engineering, etc.). Such phrases can be identified as not actually being domain-specific phrases. Such phrases can then be treated not as a single term having a unique definition and/or part-of-speech with respect to the particular specialization, but as individual words, each possessing one or more definitions or parts-of-speech.

For example, the system can parse a specialized medical text that includes the sentence "The lateral joint force dislocated his hip." The system can identify the multiple word phrase "lateral joint force" as a potential domain-specific phrase. The system can then determine that in this context, the term "lateral joint force" is a domain-specific phrase and should be treated as a single term for the purposes of text enhancement. By contrast, the system can parse a different specialized medical text containing the sentence "The destructive changes the surgeon sees in the lateral joint force him to prepare a new prosthesis." The system can initially identify the multiple word phrase "lateral joint force" as a potential domain-specific phrase. The system can then perform further analysis to determine that in this context, the word "force" should be addressed separately from the term "lateral joint." Identification of the adjacent objective pronoun "him" after the word "force" in the sentence allows the system to disambiguate the intended use of the word "force" as being separate from the term "lateral joint" rather than interpreting the entire phrase of "lateral joint force" as a single term. In this example, the identification of the pronoun "him" allows a context specific analysis portion of a text enhancement process to overrule a provisional determination that identified "lateral joint force" as a potential domain-specific phrase.

The medical language database enrichment process (or other domain-specific language database enrichment process) can be ongoing, using periodic global review of all text within a given set of texts. For example, the medical language database enrichment process can include periodic re-parsing of all textual records included in a medical record system. This periodic re-parsing can occur prior to individual patient records are presented for specific episodes of patient care. Repeating the process can help to keep the specialized, domain-specific database current with new terms, processes, diseases, medications, procedures and epidemiological terms/trends.

The system can further be used to implement a complex sentence-structure extraction process. This process can include steps that examine adjacent words and terms (e.g., domain-specific multiple-word phrases) for disambiguation, conjugation and coordination rules. Additionally, such a process can include a contingent, recursive, incremental and deferential phrase- and clause-building process, using phrase- and clause-pattern recognition criteria, combined with special masking tags to assemble confirmed clauses that are embedded within larger clauses, while continuing to build the overall sentence structure as a whole. Sentence-structure extraction processes can include extracting text specific attributes from one or more texts (such as electronic medical records, for example) and varying presentation of the texts to enhance reading accuracy, efficiency, and retention. Such processes can be performed using various techniques, for example as described in U.S. Pat. No. 6,279,017, the disclosure of which is incorporated herein by reference.

Field-specific multi-word terms can be identified within a particular passage by first performing text analysis of larger bodies of text in the field (e.g., medical field, chemistry field, electrical engineering field, etc.) and then using field-specific databases when setting up the sentence-structure extraction system that is used to identify phrases and clauses in a particular text document for enhanced visual presentation. For example, simple frequency analysis for the occurrence of multi-word terms can be performed on large bodies of text within a field or across multiple fields. A table can be constructed in which a list of all unique words in a body of text is placed into the cells across the x-axis and the y-axis. This would lead to a table having a cell for each ordered word-pair. After the table is set up, the text can be searched to identify all occurrences of ordered word-pairs, and the number of occurrences of each ordered word-pair can be stored in the table. The total count in each cell can then be analyzed, using any definition of relevant frequency that is desired. This process can also be performed directly on an individual document, as it is being operated on, enriched, and displayed for enhanced reading. The system can also use a frequency threshold to identify which ordered word-pairs should be considered multi-word terms or provisionally tagged as potential multi-word terms. The threshold can be adjusted to increase accuracy.

In some implementations, certain words or word-pairs can be omitted from the table. For example, simple function words, articles, prepositions and pronouns may be eliminated from this counting function. Such processes can also be performed using larger multi-dimensional tables to count three, four, five, or greater word phrases. For example, a three-dimensional table can be constructed to identify the number of occurrences of some or all word-triplets in a text or group of texts.

Additionally, databases of common word-pairs or multi-word terms (e.g., brute force, solar panel, nuclear energy) can be created and accessed by an enhanced text presentation system. When developing multi-word identification methods in field-specific bodies of texts, a particular word-pair may be consistently and unambiguously used only as a pair within the field, but, when the two words are used in sequence in a sentence outside of that field, there are is an increased probability that each word could belong to separate phrases. In this situation, it is important to designate that the word-pair term should only be kept as a word-pair when analyzing text within a particular field, and the system then needs to include a means to confirm whether a text being analyzed belongs to that field. One example of this is the ordered word-pair "heart failure" discussed with reference to both medical specific and non-medical specific texts above. In some implementations, even if a group of two or more words is identified as a multi-word term in a field-specific text, one or more instances of the group of words may need to be treated as individual words. Such situations can be identified based on the immediate context in which a multi-word term is used. The immediate context may have definitive disambiguating effects that would warrant that the multi-word term designation should be overridden, even within a text directed to the specific field. In other situations, an ordered word-pair or other multi-word term can be designated as always being a single term within text related to a specified field. For example, the two-word term "atrial fibrillation" can be identified as always being a single term within medical texts regardless of the immediate context of the two-word term. In some implementations, a lookup table can indicate multi-word terms that should always be considered a single term for a texts related to a specified field.

In some implementations, software configured to modify the presentation of a text passage can analyze the possible parts-of-speech of individual words within an identified field-specific word-pair (or other multi-word term), and associate a provisional pair-binding tag with the word-pair (or other multi-word term) based on the possible parts of speech of the words. For example, a pair-binding tag can be inserted between the words in the word-pair. For example, in the word-pair, "police force," the first word "police" can be a noun, verb (infinitive, transitive, non-third-person-singular, present tense), or adjective, and the second word "force" can be a noun, verb (infinitive, transitive, non-third-person-singular, present tense), or adjective. The text presentation modification software can insert a pair-binding tag between the words "police" and "force" to indicate that the word-pair "police force" has been identified as a single term, but could potentially be treated as two separate terms depending on the surrounding context.

The software can construct a new table of syntactic category combinations for the first word and second word of each pair with rules for placing a particular type of inter-word tag between the words of the provisional word-pair, and with the type of tag depending on the set of syntactic attributes of each word in the pair. Then, when the actual sentence in a body of text is being analyzed for phrase-identification, the word-pair and its inter-word tag can be used to consult the table, and the table will instruct the text analyzer to look for certain types of words that are adjacent to the word-pair.

For example, the software can analyze the following sentence: "The dangerous conditions of the area he is required to police force him to wear a bullet-proof vest." In this sentence, the syntactic attribute of the word "force" (a transitive verb) and the syntactic attribute of the unambiguous objective pronoun "him," will activate a rule in which the provisional inter-word tag that had been placed between "police" and "force" gets removed. Once this provisional inter-word tag gets removed, the overall sentence-structure extraction process of the entire sentence can proceed without the risk of an inappropriate word-pair leading to major errors in the sentence structure extraction process.

Conversely, the immediate context around "police force" could initially lack sufficient evidence to disambiguate the word "force" to its verb form, but this evidence could emerge later, after one or more recursive cycles of the sentence as a whole through a recursive, multi-dimensional sentence-structure extraction algorithm. The recursive algorithm can determine that analyzing the sentence with the word-pair "police force" as a single term leads to a sentence without a verb, and therefore the sentence is incomplete and cannot be resolved. The algorithm can then re-analyze the sentence with the words "police" and "force" analyzed as separate terms, and identify that this leads to a complete sentence and therefore that the two words should be treated separately in this context.

Text presentation modification software can also identify contextual noun-strings through a process of noun-string induction. For example, multi-noun word groups can be made up of strings of words having other possible parts of speech, (as in "wedding rehearsal banquet"), and of compound verb-preposition idioms, (as in "The burglar ran off with the old lady's purse."), which need to be resolved to be able to extract an accurate representation of the syntactic structure of the sentence as a whole. In some implementations, the contexts around the noun-string can be used to "induce" the string into a single unit of text that will then be treated as a discrete noun-segment during the sentence-structure extraction of the sentence as a whole.

This "induction" process, using both the context that is contiguous with the noun-string and remote data in other parts of the sentence, will result in the noun-string being induced into a single unit, even though the unit does not include contiguous words that had been used in the induction process. In addition, even if the criteria for such noun-segment induction are not met before the first pass of the sentence through the recursive, multi-dimensional sentence-structure building algorithms, it is possible that the definitive products of such algorithms, even if not initially reaching a complete full-sentence syntactic representation, could subsequently be used in additional attempts at noun-segment induction. These noun-segment induction rules can operate on free-standing nouns, as well as on nouns that are provisionally labeled within a field-specific noun-pair tag.

The software can also identify potential nouns that could also be verbs that, themselves, are potentially used as a verb-preposition idiom. The software can identify such verb-preposition compound verb-phrase idioms, using tables that contain known idioms in the language and the contexts of the sentence itself to "deduce" that the combination of the verb-preposition into a single verb entity is appropriate. The software can then disambiguate words that have more than one possible part of speech and assemble associated words into simple noun phrases (e.g., "the large institution"), verb phrases (e.g., "can easily be obtained"), prepositional phrases (e.g., "with the large institution"), and simple unambiguous kernel clauses (e.g., "he instructs" in the sentence: "The children he instructs are from all over town").

With this initial series of algorithms, some intermediate recursion steps are used, which then permit the assemblage of clustered phrases (e.g., a single noun-phrase and a prepositional phrases that is unambiguously included with it in a larger noun-phrase) and clustered-phrases within cluster-phrases. For example, the article "a" followed by a singular polysemous noun, such as "paint," can be combined, to create the phrase "a~paint." This new term, "a~paint," in turn, will have new attributes that the initial elements may or may not have possessed. The new term, for example, now prevents the word "paint" from interacting with other adjacent words as a potential verb. The new term, "a~paint," while still being a potential singular noun by itself, will still also have the potential to combine, distally, with a singular noun, such as bucket, to create the new phrase "a~paint-~bucket." On its proximal end, the term "a~paint" has the potential to exert a disambiguating effect on a proximal polysemous transitive verb that is a candidate predicate, such as "places," to convert the syntactic attributes of "places" from noun+verb, to verb-only, as in "The school places a~paint~bucket in each art studio."

All of these operations can be performed on a) text elements that are initially tagged with one or more syntactic-attribute tags or symbols-sets in machine-readable systems, and on b) newly formed word combinations that are given additional tags to denote the new attributes that the combination gets assigned by the structure-building rules. In this way, the sentence-structure extraction is entirely rule-based, and generates new units based on the attribute-tags of initial elements, irrespective of their meaning or size. Various other tags can be applied to the analyzed text to identify multi-word terms, parts of speech, clauses, phrases, and other attributes of the text. In some implementations, tags can be inserted into a text string using ASCII characters. For example, a "~" can be used to identify adjacent words that should be treated as a single term while "_" can be used to identify simple noun-group terms and a "*" can be used between words in a verb phrase. As another example, the symbol "^" can be inserted between words to connect prepositions with nouns. Such use of ASCII characters or other human readable characters as the tags can allow an analyzed sentence to be read by a user. The user can then use this information to modify a text analysis software to improve performance. In other implementations, tags can be inserted as metadata, or other data associated with a text string rather than being directly inserted into the text string. In some cases, the tags are machine readable but not human readable.

Figure 1:
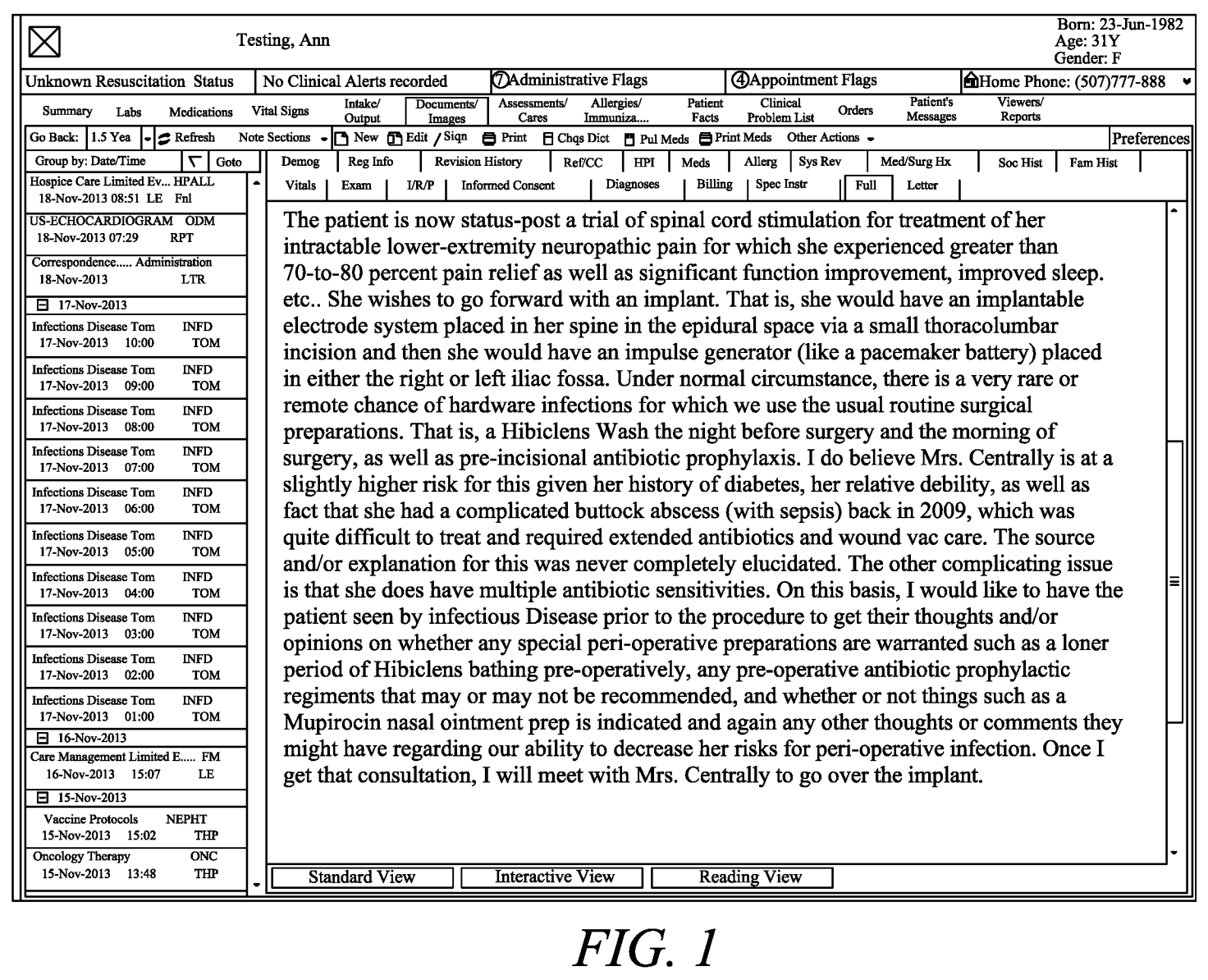

In one example process, one or more texts can be identified to a system. For example, a user can access an electronic medical record (EMR) for a patient and indicate that text presentation enhancement is to be performed for text included in the EMR. FIG. 1 shows an example of patient specific text that is included in an EMR for the patient. The text includes domain-specific terms that are related to the specialized subject matter of medical care. For example, the phrase "lower-extremity neuropathic pain" can be identified as a domain-specific multiple-word phrase. As another example, the term "Hibiclens Wash" can be identified as a domain-specific multiple-word phrase. Additional examples of domain-specific multiple-word phrases that can be identified in a specialized medical text include "chronic renal failure," "temporal lobe infarct," "post-herpetic neuralgia," "carpal tunnel syndrome," "gastro-esophageal reflux disease," and "paroxysmal nocturnal hemoglobinuria" to name a few.

Continuing with the example process, the text is parsed (e.g., by a computer system running text parsing software) to identify paragraphs, sentences, words, domain-specific multiple-word phrases, and punctuation. The text parsing software can extract, from the text, more complex syntactic structures, (including situations in which one or more clauses are center-embedded, or nested, within larger clauses or the sentence as a whole), and provide a modified presentation of the text that takes the complex syntactic structure into consideration. Paragraphs may be identified by blank lines, paragraph markers, indentation characters, tab characters, or any other suitable characteristic in the text. Sentences may be identified using grammar rules including periods, spacing, capitalization of first words, and abbreviations or the lack thereof. In a preferred embodiment reading well behaved text, a period, question mark, or exclamation point, either alone or followed by a period, followed by two spaces or end of paragraph, signals the end of a sentence.

Each sentence is tokenized into words and punctuation. Original author specified emphasis, e.g. italics or underlining, is preserved in preferred embodiments. In some implementations, the end of a word is denoted in the grammar rules by white space or punctuation. Another embodiment utilizes a hand written lexical analyzer. One embodiment stores formatting characters such as tabs and indents as punctuation. The location of a word is preferably stored as an attribute of the word, to provide links to, and searching within, the original work. Additionally, in some implementations, text enhancement engines included in the system that perform text enhancement processes can be secured behind appropriate patient-data security firewalls while still permitting text analysis to be done on a remote server, rather than on end-user devices, to support the more complex computation that is required.

A preferred embodiment also allows groups of words to be "clamped" together, and be recognized as a group of words. In one embodiment, such groups of words are recognized by the lexical scanner. In another embodiment, such words are recognized by a preprocessor preceding the lexical scanner to insure recognition as a phrase rather than as merely individual words. Clamped words, for example, "atrial fibrillation", would be recognized as a single phrase, and preferably not broken into two phrases displayed on two lines. Turning to the example shown in FIG. 1, the phrase "lower-extremity neuropathic pain" can be recognized as a single phrase, and preferably not broken into multiple phrases. Additionally, the phrase "lower-extremity neuropathic pain" can be treated as a single term for the purposes of identifying one or more parts-of-speech for the term.

Continuing with this example, identified words and domain-specific multiple-word phrases are looked up in context specific databases to determine word/phrase attributes. Such databases can take the form of or be derived from, for example, dictionaries, glossaries and tables. In some implementations, a specialized subject matter area is identified. For example, a user of the system can indicate that the text being parsed is medical related text. As another example, the user can indicate that the text being parsed is a text on an electrical engineering related subject. In another example, the system can access preference information indicating that texts being parsed by the system should be treated as medical texts. In yet another example, the text being parsed can indicate a specialized subject matter, or an information storage system that includes the text can indicate a specialized subject matter for the text. In some implementations, the identification of word/phrase attributes can be limited to texts, dictionaries, databases, etc. that are associated with the specified specialized subject matter. For example, when an EMR text is being parsed, a specialized database derived from medical dictionaries, text books, and manuals can be used for identifying word/phrase attributes for the EMR text.

Continuing with the above example, the text is further processed to determine categorical and continuous attributes. In a preferred embodiment, important categorical attributes include parts of speech, and important continuous attributes include word location, education level, pronunciation time, and syllable number, location, sound, and vocal emphasis level. Identifying parts of speech with 100% accuracy would require extensive programming to determine the real-world context of the text. Such accuracy is not required to practice the processes recited herein, as errors are of minor consequence because the reader is a human, not a machine. The possible parts of speech are first determined by looking up the word in a dictionary or glossary. In some implementations, this dictionary or glossary need only have the likely parts of speech for a word, not a definition. For example, the word "force" could be a noun, verb or adjective. As another example, the word "bleed" can be classified as a noun, verb, or adjective. As another example, the word "pressure" can be used as a noun, verb or adjective. As yet another example, the word "fracture" can be classified as a noun, verb, or adjective. A preferred embodiment stores the parts of speech attribute using a bitmap to preserve the multiple possible parts of speech. One embodiment explicitly stores an ambiguity attribute, indicating whether the word still has multiple possible parts of speech. Another embodiment uses the existence of more than a single possible part of speech as an ambiguity indication.

In a preferred embodiment, default parts of speech exist in a domain-specific dictionary and may be looked up. In a most preferred embodiment, a word set may be added to override or supplement the default set. In another embodiment, technical words are specified by user entered word sets. In one embodiment, the dictionary is a commercially available dictionary on electronic media such CD-ROM. The standard dictionary is parsed for word attributes such as parts of speech and number of syllables. As word definitions are not needed in many embodiments, storage of numerous words with associated number of syllables and parts of speech is possible. In a most preferred embodiment, the most commonly used and most recently used words are stored in fast access memory such a solid state Random Access Memory (RAM). In embodiments where dictionaries are to be hand crafted, a fast method utilizing hashing, collision detection and buckets is preferred. In embodiments where the word sets are fixed before reading, perfect hashing without buckets is preferred.

In yet another embodiment, the level of pronunciation emphasis is derived as an attribute depending in part on the part of speech. In a most preferred embodiment, pronunciation emphasis is categorized as primary, secondary, and none. In one embodiment, the pronunciation time and actual sound, e.g. as found in a sound file, are also retrieved from the dictionary or glossary and stored as attributes of the word.

The process further includes disambiguation between multiple parts-of-speech. In one embodiment, a microgrammar routine is used to determine the likely parts of speech. A microgrammar routine utilizes adjacent or nearby words to more accurately determine the most likely part of speech for a word. For example, the word "pressure" in the phrase "apply pressure" would likely be a noun as it is preceded by a verb. As another example, if a word could be either a noun or verb, and the word is preceded by "could", "will", "shall", or "to", then the word is likely a verb. If the word "pressure" were preceded by "will", the word is likely a verb. In another embodiment, all disambiguation is done simply by choosing the statistically most likely use of the word. In yet another embodiment, there is no automatic disambiguation, only manual disambiguation using human editing. In a preferred embodiment, an attribute of ambiguity is stored for each word, indicating whether multiple possible parts of speech still exist after disambiguation. In yet another embodiment, an ambiguity attribute is not stored but derived from the existence of multiple possible parts of speech stored for a word. In one embodiment, ambiguity is inferred from the visual display of striped or alternating text colors associated with each part of speech. For example, if verbs are orange and adjectives are yellow, then a possible verb or adjective could have alternating yellow and orange stripes or text characters.

The process additionally includes determining primary folding points by applying primary folding point rules. Folding points are text dividing points located between letters. In a preferred embodiment, folding points are classified as primary and secondary. Primary folding points are determined using primary folding rules which determine primary folding point locations based on punctuation marks. For example, a comma in a sentence can be used to identify a primary folding point. Primary folding points divide text into "Super-phrases". In a preferred embodiment, primary folding points are located at every comma, colon, semicolon, and left parenthesis, brace, and curly bracket. The folding point location can be stored as an attribute in a node in a linked list of nodes forming the enriched sentence.

Secondary folding points are determined applying secondary folding point rules. In preferred embodiments, secondary folding points and rules are ranked in a hierarchy and secondary folding rules accept parts of speech as inputs. In a most preferred embodiment, secondary folding rules include as rule inputs attributes of the text content of the text segments and phrases being processed. For example, a secondary folding point may be called for by a segment of text exceeding a reader preferred maximum text segment weight even though a maximum text segment length has not been reached.

Continuous attributes such as phrase difficulty, density, complexity, power and pronunciation time may be used as inputs to a rule modifying the ranking established by a table using parts of speech alone to determine secondary folding part rankings. For example, a segment of text having a weight greater than 35 percent above the text average would have a Class rank of 1 assigned regardless of the rank otherwise called for by the table. In one preferred embodiment, phrase weight or power is used exclusively to determine secondary folding point rankings, rather than solely parts of speech.

In an alternate embodiment, folding rules call for folding based on the number of characters on the line, and the parts of speech are displayed using colors corresponding to a word's part of speech. The later embodiment may not offer the advantages of cascading, but does offer visual display cues based on text content.

Primary folding rules are applied first, followed by secondary folding rules, applied in order of the folding rule rank. Some preferred embodiments use either phrase weight or power to determine secondary folding point rank rather than solely using parts of speech. A most preferred embodiment allows reader entry of a preference for parts of speech or phrase weight/power determination of secondary folding point ranking. Some readers prefer text segmentation based on structure, while others prefer text segmentation based on complexity or estimated time to read a text segment.

In a preferred embodiment, secondary folding rules are applied only until a limit is reached. This limit is often the minimum line length. In one embodiment, where the application of a secondary folding rule to a Super-phrase would result in a Mini phrase length less than the minimum specified line length, the folding rule is not applied and no further folding rules are applied to that Super phrase. Conversely, when no folding point would otherwise exist in a line exceeding the maximum line length, a collapse rule is applied, forcing the folding of the text into two lines. When all Super-phrases are to have no further folding rules applied, the folding process is complete. In some implementations, identified folding points are marked using tags associated with the text to identify the locations of the folding points.

In some cases, parsing of a text can include identifying phrase weights for various phrases. Phrase weight is a derived attribute of a phrase (text segment or potential text segment) giving some measure of the amount of material in a phrase. In one embodiment, the phrase weight is simply the number of words in a phrase. In preferred embodiment, phrase weight includes phrase density and phrase complexity. Phrase density can include the number of technical words or number of words exceeding a certain grade level. Phrase complexity can include the number of spelling similarities between words in a phrase, number of ambiguous words, and total weight of reader weight specified words.

Natural language syntax can be characterized as having at least five dimensions that can be extracted from machine readable texts.

The first dimension is the unique linear sequence of words in a text string, and the associated possible parts of speech of each word in the sequence; this first dimension of syntax is extracted during tokenization steps in text processing, using inter-word spaces to demarcate words, and databases that store all possible parts of speech of each word. The pre-identification of provisional domain-specific multi-word terms, which can be added to the database used to assign all part-of-speech attributes of each term, is part of the first dimension of sentence structure extraction.

The second dimension of syntax is the identification of serial sequences of words, or word groups, with a part-of-speech assigned to the group based on analysis of the sentence-specific context. This second dimension of syntax is extracted by several of the processing steps described so far, including: a) context-based over-riding of domain-specific provisional multi-word terms; b) noun-string induction; c) verb-preposition compound phrase deduction; d) use of and possible combination with adjacent words for the disambiguation of words with multiple possible parts-of-speech into context specific definitive part of speech; e) verb conjugation. The second dimension of syntax is extracted by simultaneous interrogation of the attributes of multiple contiguous elements (words or word groups) in the sentence string, which recognizes potential word-groups based on rules applied to the syntactic properties of each element, adding additional tags or labels to the newly recognized word group; then the process recursively re-interrogates the transformed string using the new set of elements and their inter-element relationships. The text enrichment products of this second dimension of syntax extraction can be processed as discrete units using inter-word markers or tags.

The third dimension of syntax is the set of boundaries separating noun phrases, verb phrases and prepositional phrases, with each such phrase potentially containing other constituents. This third dimension of syntax can be extracted through a process that includes: a) identification of phrase-head words and the part-of-speech attributes of each phrase-head word, including attributes of person, case, tense, and transitivity; b) coordinating conjunction recognition frames to identify both heads of compound noun and verb phrases; c) simple prepositional phrase absorption rules that incorporate prepositional phrases into the larger noun or verb phrases that they modify; and d) noun phrase absorption rules that incorporate noun phrases, as direct and indirect objects, into verb phrases that have transitive properties. The text enrichment products of this third dimension of syntactic extraction can be processed as discrete units using pen-phrase brackets with tags denoting the anterior and posterior boundary of each phrase.

The fourth dimension of syntax is the clause. This fourth dimension of syntax is extracted with clause pattern recognition rules, with an interrogation frame that simultaneously examines the attributes of adjacent phrases, to determine if criteria of case agreement are met. The text enrichment product of this fourth dimension of syntax is a clause-unit, which can be processed with encapsulation tags at the anterior and posterior boundary of the clause. When all of the elements of an entire sentence are encapsulated within a single clause, the syntactic structure extraction process can conclude.

The sentence structure extraction processes described so far can be utilized to identify the first four dimensions of syntax. The fifth dimension of syntax is the reciprocal relationship that clauses can have within phrases and that phrases can have within clauses. For a noun phrase, an embedded clause can be a relative clause that qualifies or modifies the semantic properties of the noun phrase. For a verb phrase, an embedded clause can play the role of a sentential complement. In even more complex sentence structures, center-embedded clauses will lie in between the proximal (subject) and distal (predicate) components of one or more larger clauses that contain them.

The nub of the problem in extracting this fifth dimension of syntax structure is this: a clause is extracted with clause pattern recognition algorithms by creating and closing a structure around a closed candidate noun phrase adjoining a closed verb phrase with appropriate case and form agreement conditions between the noun phrase and verb phrase.

However, in some cases, a phrase can itself contain a smaller inner clause, and such a smaller inner clause can contain a phrase that itself will contain yet another inner clause; and a clause inside of a phrase cannot be closed until all of the phrases in it are closed, and the phrases in a clause cannot be closed until the clauses inside the phrase are also closed. In other words, there is a phrase versus clause stalemate that mere phrase-based analysis or simple clause pattern recognition analysis is not able to resolve.

This fifth dimension of syntax requires an analysis across all of the noun phrase, verb phrase and prepositional phrase and simple clause products that are extracted with the first four dimensions of syntax extraction. In some cases, the fifth dimension of syntax requires different enrichment tags and operations. This fifth dimension syntactic-structure extraction-process addresses the essential dilemmas in recursive sentence structure.

The first dilemma is that. if a smaller inner clause is embedded in a larger outer noun phrase, this larger outer noun phrase will not be able to participate, itself, in algorithms for larger clause pattern recognition that would combine the larger outer noun phrase with an adjacent verb phrase (for which there is appropriate case agreement) until all of the components of the smaller inner clause are identified and the smaller inner clause is then fully encapsulated and absorbed into the larger outer noun phrase as a constituent. Similarly, a larger outer verb phrase, (when being considered, based on case agreement, for clause pattern recognition with an adjacent, proximal noun phrase), will not be able to include all of its constituents, as a single verb phrase unit, if the larger outer verb phrase has an embedded smaller inner sentential complement clause in it that has not yet been fully recognized, itself, as a discrete clause and encapsulated. Additionally, noun-less verb-phrase units, (i.e., past participle verb phrases, gerund verb phrases, and infinitive verb phrases), which may have adjectival or adverbial properties that may modify noun phrases or verb phrases, can also contain sentential complements, and therefore will not be absorbable into the larger noun phrase or verb phrase that contain them until after the embedded sentential complement has been recognized by clause pattern recognition and encapsulated. Similarly, each verb phrase in a pair, or more, of a compound verb phrase, can have their own embedded clauses that must be extracted, encapsulated, and absorbed into the verb phrase before the verb phrase pair can be joined together, to then participate in clause pattern recognition with an anterior, case-agreement appropriate noun phrase.

This fifth dimension of syntax is extracted by the combination of several operations that are qualitatively distinct from the first four dimensions of syntax extraction. First, a new set of text enrichment phrase markers, called envelopes, is used that not only denote the proximal boundary of each type of phrase, (noun, verb, and preposition, with additional data for person, case, tense and transitivity), but also denote, in the anterior marker, whether the distal boundary of the phrase has been identified yet (showing that the phrase is "closed") or whether the distal boundary remains indeterminate (because it is awaiting closure of other phrases or clauses that will be embedded in it). Second, for noun phrases, even after the noun phrase envelope has become closed, an additional type of label for the envelope (e.g., a marker or tag) can used to denote that the noun phrase has encountered the anterior boundary of the envelope of a verb phrase that would be a candidate predicate in clause pattern recognition, but the envelope of the verb phrase itself has not yet become closed because it has other potential downstream elements that may be or may contain another embedded clause or noun-less verb-phrase that is not yet closed; this additional envelope marker (used to denote a closed noun-phrase that has "touched" a potential verb phrase mate for clause pattern recognition that, in turn, is still not yet closed) is used to prevent that same noun phrase from being absorbed, as an object, into an upstream transitive verb phrase.

The next step in this fifth dimension of syntax structure extraction is the use of a multi-segment interrogation frame over sequences of phrase envelopes, which examines the additional phrase-envelope markers, and simultaneously evaluates the closed, open, and closed-with-mate-touching states of the phrase-envelopes. An enriched text string gathering mechanism is then used that is governed by rules based on multiple attributes of the envelopes and their phrases, including: a) whether the phrase-envelope is open, closed, or closed-with-mate-touching; b) the person and case of the noun phrase and; c) the person, case, tense, and transitivity of the verb phrase; d) other special attributes for noun-less verb-phrases and pairs of verb phrases in compound verb phrases; (e.g., infinitive, past participle or gerund form, and transitity); e) the presence of coordinating conjunctions at the head of verb phrases; plus f) the presence, at the end of all phrases, of a sentence-concluding punctuation mark.

These fifth dimension interrogation and gathering rules can include principles such as: a) a phrase cannot gather into itself an immediately distal phrase until after the distal phrase is itself closed; b) a noun phrase cannot gather a verb phrase into itself if the verb phrase is a candidate, case-agreement clause mate, but the encounter will result in the noun phrase becoming closed and marked as having touched its mate; c) encounters between a noun-phrase and an immediately distal verb phrase that have incompatible case agreement properties will result in the noun-phrase becoming closed without a touched-verb-mate marker; d) verb-phrases that are not potential noun-less verb phrases cannot be gathered into other phrases but can only join, with a case-agreement compatible closed noun-phrase, to form a clause; e) if the gathering process for a proximal verb phrase envelope encounters, while assessing whether to gather the next phrase, the proximal boundary of another verb phrase that is not a potential noun-less verb phrase, then the envelope of the proximal verb phrase will close. The text string interrogation and gathering apparatus will also enable a clause, (which becomes formed using clause pattern recognition criteria, including when a closed noun phrase envelope is immediately proximal to a closed verb phrase envelope that has appropriate case agreement with the noun phrase), to become gathered into a larger noun phrase (as a relative clause) or into a larger verb phrase (as an sentential complement), which then permits the larger noun phrase and verb phrase to close.

In this way, the fifth dimensional syntax extraction process makes it possible for embedded relative clauses and clauses that serve as sentential complements to become absorbed by the larger noun phrases and verb phrases that contain them, respectively, which ultimately enables the entire sentence to be encapsulated as a single clause.

Importantly, the overall, recursive and incremental syntactic structure extraction processes for the sentence as a whole proceed across multiple dimensions in parallel, with various segments of a sentence undergoing syntax extraction steps in any of the second through fifth dimensions, and with recursion going back, (after the fifth dimensional extraction has completed the absorption of an encapsulated clause into a larger noun or verb phrase envelope), through another third or fourth dimension extraction process for additional phrase and simple clause extraction processes. In this way, a sentence-specific mosaic of enveloped, encapsulated, bracketed and clustered structures-within-structures incrementally emerges, until the ultimate encapsulated structure, i.e., the clause of the sentence as a whole, is built.

This fifth dimension of syntax is also essential to be able to conclude if the initial use of a domain-specific multi-word term will result in the extraction of the entire sentence structure as a single clause. By adding a procedure that examines the final state of syntactic extraction processes, after each cycle in a recursive system, with the final state of the cycle that preceded it, and by examining such states using clause pattern recognition criteria, it is possible for the extraction process to determine that the use of the domain-specific multi-word term led to an incomplete sentence structure extraction. This result can than be used to remove the domain-specific multi-word tag and then send the sentence through series of multidimensional sentence structure extraction processes again.

In some implementations, as discussed above, analysis of a text passage includes recursive analysis of the text to identify multi-word terms, parts of speech, folding points, and other attributes for the text. For example, sentences and other text strings in a passage are analyzed to identify various clauses and then recursively analyzed to group the clauses into larger clauses. Such recursive analysis can be used by a text presentation modification system to identify hierarchical folding points for sentences and other text strings. Steps of such a recursive process can include identifying the heads of phrases, with encoded secondary text tags for special categories of nouns (case and person), verbs (case, transitivity, and tense), and prepositional phrases for a given string of text. The process can then "absorb" allowable text segments distal to the head of the phrase, (i.e., scanning and "gathering" distal segments of the enriched text, starting with the head of the phrase and interrogating the attributes of the enriched text's word units and word-group units distal to the head phrase, based on their respective categories and enriched tag information, and placing the gathered units into special encapsulating tags of a multi-unit segment). The process then identifies boundaries distal to the head of the phrase that prohibit further absorption of the text string by the phrase.

The process can then label identified phrases as "open" or "closed" based on their analysis and encounter with distal boundaries that prohibit further absorption. In some cases, phrases identified as "open" can be converted to "closed" phrases in response to the process encountering a distal text segment or element that meets certain criteria. The process can combine phrases that meet criteria for comparable phrase categories and which have appropriate conjunctions ("and" or "or" or "but") between them, but only after each of the comparable phrases has been identified as closed. The process can recognize clause patterns (Clause Pattern Recognition or CPR) in the groupings of appropriate noun-verb relationships based on case agreement, after the noun-phrase and verb-phrase have both become "closed" and have been identified as touching each other. The process can then treat the recognized embedded clause as "transparent" or "cloaked" so that it can also be absorbed by other "open" phrases, and so that it will subsequently be "passed through" by the text string interrogator and will therefore essentially not participate in any further interrogations.

The system can further enrich the text with multi-hierarchical sets of nested phrase bracket tags, embedded clause encapsulation tags, and multi-word cluster tags, through recursive interrogation of steps in word-group clustering, phrase-bracketing, embedded clause-encapsulation, and meta-phrasal and clause gathering and enveloping, using context-specific rules that redirect the interrogation to other sub-processes until full-sentence clause structure is extracted or until inter-cycle state comparison of the tag sets for the sentence demonstrates no net state change between cycles.

As another example, a text presentation modification system can analyze the sentence "The runner says her left ankle joint aches after running two miles." The process of analyzing the sentence can begin by tokenizing each word and punctuation mark in the sentence. Some or all of the words in the sentence can then be enriched with one or more attribute tags identifying particular aspects of the word. For example, attribute tags can identify that a particular word (e.g., "two") should provisionally be included in the same clause an adjacent word (e.g., "miles"). The two word phrase "two miles" can be identified, for example, through application of a number-unit rule that identifies numbers as likely being included in multi-word phrases. As another example, the process can initially identify the term "joint aches" as a provisional two word phrase and insert a tag indicating as such (either associated with one or both of the words "joint" and "aches" or inserted between the two words). Other words in the sentence can be associated with tags identifying the parts of speech for the words, or other attributes of the words or word phrases.

Recursive analysis by the process can determine that the provisional identification of the word-pair "two miles" as a single term is correct and treat the term two miles as a single term for purposes of modified text display. The recursive analysis can also determine that treating the word-pair "joint aches" as a single term leads to a sentence without a verb, and therefore that the provisional identification of the word-pair "joint-aches" as a single term is incorrect. The system can then remove the provisional tag identifying the word-pair "joint aches" as a single term and treat the two words "joint" and "aches" as separate terms with their own parts of speech. By contrast, if the word-pair "joint aches" appears in the sentence "Runners who present with joint aches after longer distances should be evaluated for cartilage tears" then the word-pair "joint aches" would properly be treated as a single term in such a case.

In some implementations, after text has been parsed, the text is varied into a new presentation format. Various tags associated with the text can be used to vary the presentation of the text. This text variation can include displaced horizontal justification of sentence segments. Horizontal justification rules specify the horizontal justification of a line of text relative to the line above. Justification can include the justification type for the line or phrase being positioned, i.e. right, left, or center justification. Justification can also include the text portion of the line above from which the justification is measured, i.e. the entire line of text versus one phrase, the point of that portion used, e.g. left-most, right most, or center. Horizontal justification in one embodiment is simply measured within the line being positioned rather than relative to the line above.

In a preferred embodiment, the first phrase on a line is center justified, measured from the center of the last phrase in the line immediately above. In another embodiment, the entire line of text is center justified below the center of the line of text above. In yet another embodiment, the text segment "center of gravity", calculated using the difficulty of each word, is used as the text segment center for justification purposes.

A descent angle can be used to define the amount of horizontal displacement for each new line, modifying the horizontal position called for by the horizontal justification rules alone. By definition, each text segment is presented on a new line. In a preferred embodiment, the descent angle is specified in units of characters. The descent angle and horizontal justification at least partially determine the "text cascade" down and across the screen in preferred embodiments. A descent angle may be zero, meaning that, without more, the text segment horizontal position is determined by the horizontal justification rules alone. A descent angle can be left, where the line below is to be shifted left relative to the line above, or right, where the text shifts right.

In one embodiment, the decent angle in a constant for each new line. In a preferred embodiment, the descent angle is a function of the text segment weight of the line above. In another preferred embodiment, horizontal justification rules call for center justification below the center of each line immediately above, and the descent angle is calculated to present a substantially straight path, when all text lines are presented, from center of line to center of line, from upper left to lower right on the display surface.

In a preferred embodiment, the inputs to descent angle rules include attributes of the text in the line above. In one preferred embodiment, inputs include the reason for folding the line above, i.e. primary folding point, secondary folding point, or collapse rule. In a preferred embodiment, a more positive descent angle is called for when the line immediately above folded due to a primary folding point than a secondary folding point. In another preferred embodiment, the inputs include the text segment weight of the current line and the line above.

It is recognized that the horizontal justification rule could call for left justification and measuring horizontal displacement from the left margin, as well as a zero descent angle, combing to result in left justified text on each line. It is also recognized that horizontal text positioning can be accomplished in numerous equivalent ways to the above example. In particular, calculations of text position can be accomplished by first justifying then shifting, or first shifting then justifying with equivalent results.

In one embodiment, gaps are associated with folding points whose locations have been determined, but because of other rules, remain on the same line and do not cause folding. A gap of zero or more spaces is added after a folding point where that folding point has failed to cause new line creation. In a preferred embodiment, the gap length is a reader determined parameter, where a gap length of zero results in a no gaps being created. Gaps allow a visual cue as to the existence of phrases even where the phrases have not caused new line formation.

The parameters, attributes (e.g., as identified by tags associated with a text string), and folding rules can be used as input to the horizontal displacement rules. The horizontal displacement rules determine the horizontal location of the text segment. In a preferred embodiment, horizontal displacement rules include both horizontal justification rules and descent angle rules. Horizontal displacement in this embodiment is the sum of the results from the horizontal justification rule and the descent angle rule. In an easy to implement embodiment, the horizontal displacement rule is simply the descent angle as applied to the center justified text segment. Such an embodiment does not utilize the folding rule terminating the preceding text segment as input and provides minimum eye movement while reading the sentence cascade. Another embodiment adds left descent for preceding Class 1 folding points, and right descent for preceding Class 3 folding points. A preferred embodiment allows reader specified additional right or left displacement for folding points, including reader entered values for primary folding points, and each class and subclass of secondary folding points. One embodiment stores the added displacement in a table in units of characters. With the horizontal displacement determined, presenting the text remains.

After the various folding points and horizontal displacement rules have been derived, the codes needed to create a properly displayed text segment are created. For example, where the reader specifications require coloring technical words red, and the enriched text indicates a word is a technical word, an escape sequence may be created that will be interpreted by the display step as requiring red text. Similar coding may be required for animation. The enhanced text may be stored at this point for later display.

The enhanced text is then presented on the display device, one text segment per newly formed line. The enhanced text can also include the animation, background color, text color, tagging, and presentation rates discussed above. In a preferred embodiment, the background color is presented as a function of the sentence and paragraph positions. In some implementations, the enhanced text is stored for later display. The enhanced text can be stored with additional visual attributes and other tags for features for improved reading performance and retention, such as phrase-based cascading, color-high-lighting of certain terms of parts of speech, scroll-over image pop-ups, links to other resources, audio word and phrase pronunciation, etc.

In some implementations, a text display system can have a level of multidimensionality that corresponds to the dimensionality of syntactic structures that have been extracted from a text during syntactic analysis, and can also utilize the structural tagging data that accrued and were kept with the source text during the structural extraction process as a means to render this syntactic multidimensionality in perceptible patterns in the text display. Such multidimensionality can be expressed by changing various display aspects of words within the text such that the multidimensionality can be conveyed within a two dimensional display area.

For example, if the only structure in the text is a preservation of the serial order of all of the words in a sentence, then standard linear text, with undifferentiated word-wrapping at the end of an available column width, is the only dimension required. However, if text analysis identified multiple phrase boundaries, (without necessarily specifying a hierarchical relationship between phrases), then a two dimensional presentation could involve putting an extra space or other indicator (such as a tag) between each phrase on word-wrapped formats, or placing each phrase on its own line, but without any indentation of the new line.

If the syntactic extraction further differentiated the text structure, identifying major phrase categories (e.g., subject-noun, object-noun and predicate-verb phrases) and additional subordinate (prepositional) phrases that might be contained by them, then additional indentation of the phrases on each line could be used to identify the hierarchical relationship between the major phrase and the constituent phrases that the major phrase contains.

If the syntactic extraction process further identifies embedded clauses in a sentence (such as relative clauses modifying a noun, or sentential complements playing the role of the object of a verb), then yet another presentation dimension is important to denote the extraction of the embedded clause, even while the dimensionality of major phrases (noun-subject, verb-predicate, noun-object) in the embedded clause, and of constituent phrases (prepositional phrases modifying nouns or verbs) within the major phrases is preserved and transparently conveyed. The representation of such embedded clauses can utilize other dimensions in addition to the initial two, the y (row number) and x (indentation on a row) coordinates of the display; for example, a font style choice (e.g., shifting from Times to Arial) or size (dropping from 12 to 10 point), or a slight change in the color of the text font or background surrounding the text of the embedded relative clause, could be used to depict this added dimension of text structure extracted. Various other modifications of the visual display of the text can be used to display multidimensionality including bolding, underlining, italicizing, change in width or height, change in color, change in position, or highlighting.

Figure 2:
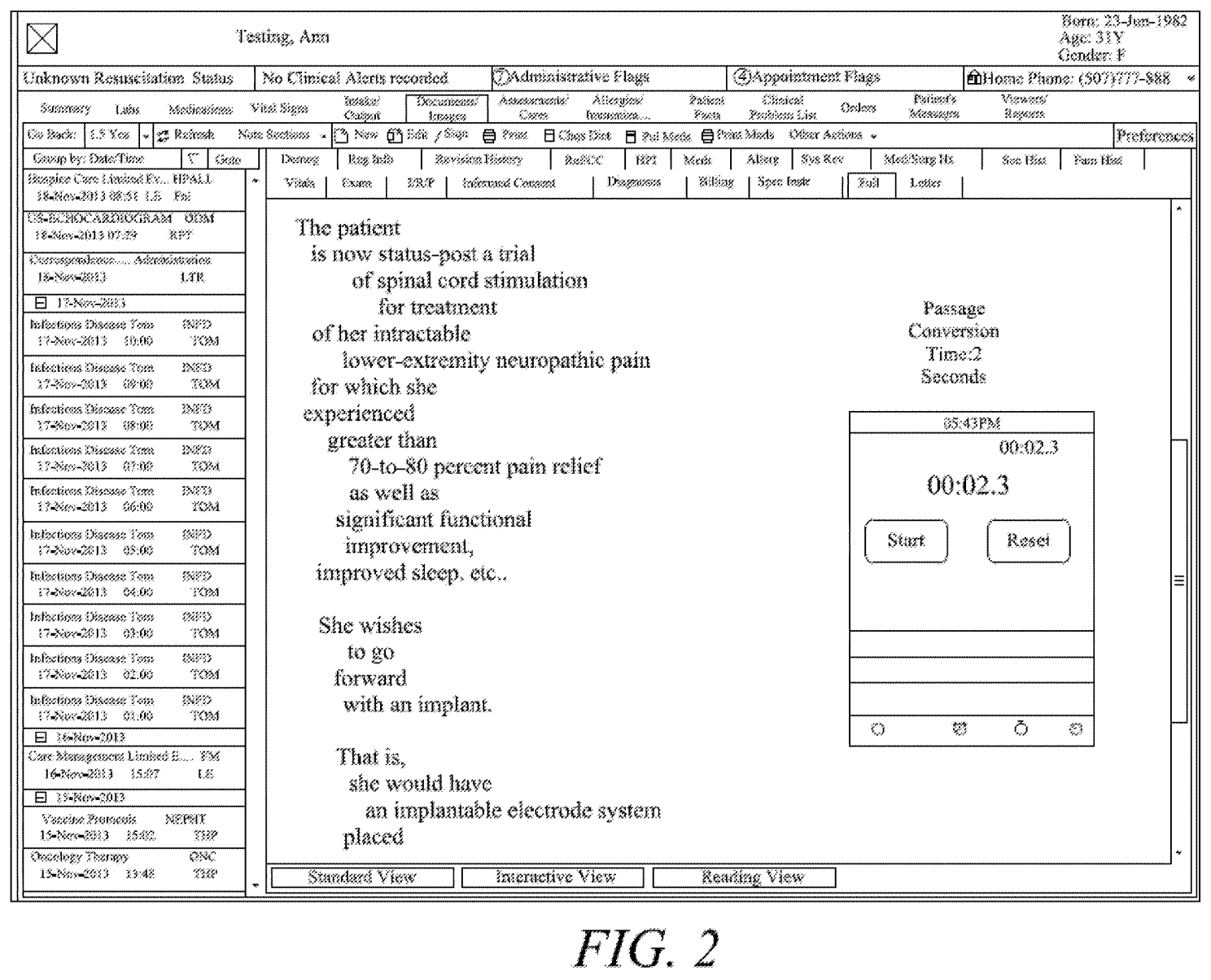

FIG. 2 shows an example of graphic user interphase for the EMR that includes a portion of the text shown in FIG. 1 that has been reformatted from its original format into an enhanced format for the purpose of improving reading accuracy, efficiency, and retention. The sentences of the text have been broken into text segments of various lengths along various identified folding points. Each text segment is located vertically below the previous text segment in the same order as in the original text shown in FIG. 1. Additionally, each text segment is horizontally displaced (left or right, and by a specified length value) with respect to the previous text segment according to determined horizontal displacement rules. The modified presentation of the text can enhance reading speed for a reader, as well as reading accuracy and retention. Display software configured to modify the presentation of a text passage, as shown in FIG. 2, can improve reading accuracy and efficiency for users reading the reformatted text by accurately representing a sentence's complex syntactic structure. This includes ensuring that field-specific multi-word terms do not interfere with accurate, multi-dimensional syntactic structure extraction during enrichment steps, and keeping field-specific multi-word terms intact on single rows in the modified displayed text.

Text presentation modification software can additionally be utilized to modify text presentation by extracting field-specific multi-word terms and enriching such terms with removable, context-contingent labels based on part-of-speech attributes of the individual words in the multiword term. The software can also identify center-embedded clauses (i.e., clauses embedded within larger clauses) through a recursive process of identifying multi-word clauses within a sentence or other passage of text, and then identifying shorter multi-word clauses within the initially identified multi-word clauses. In some implementations, an embedded clause can be displayed in a different format from surrounding text (such as a different font, bolded, italicized, underlined, or in a different color). Implementation of such processes can lead to recursive, interweaving interaction between multi-word term coining and multi-dimensional sentence-structure building.

Upon displaying a visually modified text presentation for a text passage, the software can accept user input from a reader and use this user input to further dynamically modify the displayed text. The user input can include information that is specific to the reader. For example, the user can indicate a preferred text segment length or difficulty (e.g., on a numeric scale or other scale) and this information can be used to modify the text presentation for the text passage. The user may also change other information that can lead to a modification in the presentation of the text, including changing margin widths or entering a preferred display area width or size. Such user input can, in some implementations, be received in the form of a user resizing a display window in which the modified text is displayed using controls for the display window. Other information (that could be provided by the user, or determined by a computing system) that can be used to modify the presentation of the text can include the size of one or more display screens on which the text will be displayed. The size of the display screen can be conveyed in terms of absolute size (e.g., width and height in centimeters), pixel size, aspect ratio, or another suitable unit of measure.

Initiation of the process for enhancing medical texts (such as EMRs) and other subject matter specific specialized text can be done by an author of the text (e.g., a medical caregiver entering information associated with a patient) by a reader of the text, or can be automatically performed if one or more criteria is met. For example, all text stored within the system that meets a threshold length can be automatically enhanced by the system using one or more of the above described processes. The enhanced medical text can then be stored in a form that is readily accessible when end-users attempt to access the original text form.

In some implementations, users are allowed to modify the visual presentation of enhanced text. For example, the system can allow individual users to position the modified text on a display screen at particular positions and in variable sizes (including fields optimized for mobile tablets and smaller screens), to permit the user to combine reading activities with other data usage and input in the text with appropriate accuracy and efficiency.

The system can also be implemented to vary the presentation of text, including varying the presentation of one or more enhancement effects, based on a type of reader that is reading the text. For example, a first type of enhancement can be applied when a physician is reading a text while a second type of enhancement is applied to the same text when a nurse is reading the text. As another example, different types of text enhancement can be used for a reader that is a surgeon versus a reader who is a general attending physician. As yet another example, a first type of text enhancement can be applied when a lawyer is reading a text while a second type of text enhancement is applied when a paralegal is reading the same text. Based on the reading proficiency level and expertise of the reader, the apparatus could automatically include additional presentation effects (e.g., gloss-over images or synonyms for anatomic terms or highlighting of domain-specific extracted terms).

In some implementations, the system can compare the skill level, training level, or knowledge area of the reader to the skill level, training level, or knowledge area of the writer of the text to determine what type of enhancement to apply to the text. For example, the system can vary the display and text presentation effects for a medical text depending on whether the reader is a physician in the same specialty as the author of the text or a physician in a different specialty from the author. Additionally, different enhancement levels can be used for differing levels of experience. For example, different text enhancement types can be used for different readers such as if the reader is a resident, medical student, mid-level provider, or even a patient who may have no medical training.

FIGS. 3A-3B show an example of a text that is enhanced using two different enhancement levels for different readers. Both figures show different enhancements of the following text:

"Normally we do this as an outpatient but in her case because of her general debility I would do her as an inpatient and then we would more than likely try to see if we can make arrangements for a perhaps one to two week stay in an extended-care facility just because she is limited with her mobilities and transfers and wound care abilities."

FIG. 3A shows a first enhancement of the text for a first reader, while FIG. 3B shows a second enhancement of the text for a second reader. The two different enhancement levels can be based on one or more differences between the readers, including preferences indicated by each reader, reading ability of each reader (e.g., reading ability as measured by the system) or familiarity of each reader with the subject matter. For example, the version in FIG. 3A could be an enhancement for a medical student while the version in FIG. 3B could be an enhancement for a physician who has been practicing for multiple decades.

In some implementations, screening criteria are applied to a text that is targeted for enhancement to identify natural language sentences within the text and differentiate the natural language sentences from other portions of the text. For example, tables, lists of demographic information, lists of medications and allergies, lists of prior medical conditions and operations, lists of related surgeons, indications, or pre-operative diagnoses and procedures can be identified as non-natural language sentences and not included in a text enhancement process. In some implementations, the system can skip sections that are not natural language sentences until a narrative description portion of a text is identified.

This identification and differentiation process can allow the system to perform text enhancement for the identified natural language sentences to allow the natural language sentences to be more easily and quickly read and understood while leaving other portions of the targeted text in an original format. For example, a specialized text such as a medical text might include lists of medications or other text information in list or table form as well as natural language sentences. The system can identify the natural language sentences and perform text enhancements on the natural language sentences while leaving the lists of medications in their original format. As another example, a specialized legal text might include natural language sentences interspersed with case citations. The system can differentiate the natural language sentences from the case citations, then perform text enhancements for the natural language sentences and present the natural language sentences in an enhancement format while leaving the case citations in their original format. The system can also differentiate natural language sentences from other portions of an electronic text document such as images, numerical laboratory results, text entry fields, lists of medications, and the like. The system can ensure that modified medical text is appropriately integrated with these other fields of data to ensure a reliable and efficient reading experience for a medical professional or other professional reading the modified text.

For example, the enhanced text can convert a wide rectangle of block text into a narrower strip of cascading-phrase text. With the narrower strip of enhanced text, one could place an image (e.g., a CT or Chest x-ray image) adjacent to the text strip, occupying two thirds of the screen, and the text strip itself could be scrolled up or down, while the image remains in the same position. These relationships could be dynamically modified depending on whether the display screen is in a portrait or landscape position. Landscape mode could also present 3 columns of enhanced text (each narrower columns) if the document contained no images, but then substitute one or two columns of text with an image, as needed.

Turning to FIG. 4, the enhanced text formatting system presents texts in short rows, to reduce visual crowding. However, rather than randomly breaking text based on the width of the screen, the process identifies the most salient grammatical boundaries, and places a hierarchy among them, breaking text at the highest hierarchical boundary first, then progressively shortening segments, as required, until all rows are shortened to one or two visual eye-spans (e.g., between 5 and 30 characters). An example hierarchy for identifying grammatical boundaries and breaking text is shown in FIG. 4.

Figure 5A:
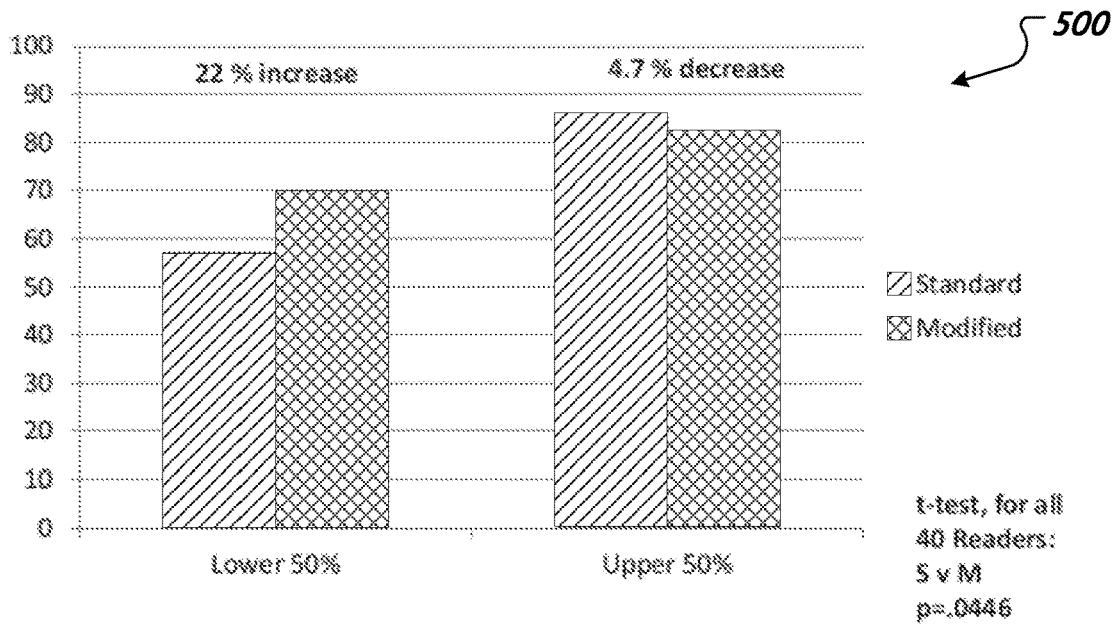
FIGS. 5A-5B show graphs indicating improvement in reading retention, accuracy, and efficiency due to implementation of varied presentation of texts.
Figure 5B:
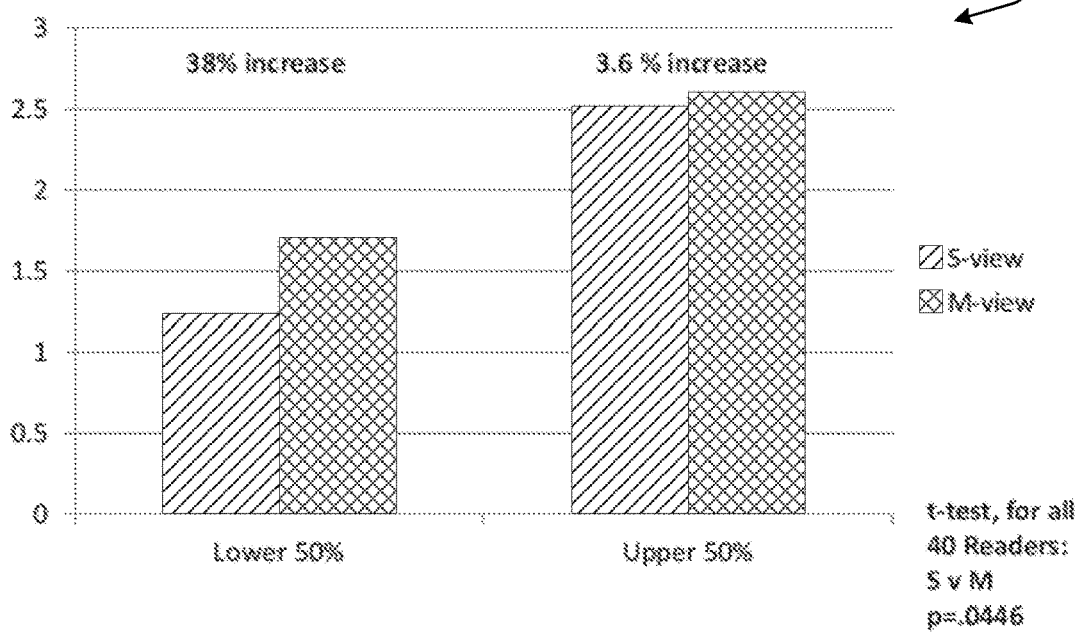

FIGS. 5A-5B show graphs 500 and 510 (respectively) indicating changes in reading retention, accuracy, and efficiency due to implementation of the above described techniques for varying text presentation. The graphs 500 and 510 show the effects of varied text presentation in an experiment conducted using 40 participants from a medical graduate program. The participants were presented with 10 medical text passages drawn from various electronic medical records. The average length of the 10 passages was 412 words. Each participant read half of the 10 medical text passages in the original format, and the other half of the medical text passages in the modified format (i.e., varied text presentation), such that 20 participants read each medical text passage in the original format and 20 participants read each medical text passage in the modified format. Upon completion of a medical text passage, participants were presented with three multiple choice questions related to the passage, for a total of 30 multiple choice questions presented to each participant.

As shown by graph 500 in FIG. 5A, participants in the lower 50% of reading retention showed a 22% increase in retention when exposed to modified text passages over text passages in their original format. However, a 4.7% decrease in retention was shown for participants in the upper 50% of reading retention for modified text passages verses original format text passages. FIG. 5B shows that reading efficiency, measured as retention-adjusted speed, increased for both categories of participants, with an efficiency increase of 38% for the lower 50% of reading efficiency participants for modified text passages over original format text passages. Participants in the upper 50% of reading efficiency showed a 3.6% increase in reading efficiency when reading modified text passages verses original format text passages.

In some implementations, the system can additionally employ a user-monitoring process that can track each individual user's time when reading medical texts, while reporting back to the end-user their word per minute reading rate, to help the end user determine optimal conditions for whether or when to use reading performance tools. The step can also provide standardized opportunities for an individual to compare their own reading performance with or without additional reading performance tools. This can serve to help a user see the benefits of using the text enhancement system. The user-monitoring process can also include camera-based equipment to track users' eye-movements while reading, to capture whether frequent regressions or re-reading is taking place, such as when a reader is fatigued, which could prompt a suggestion from the computer to the user to try one or more reading enhancement or reading assistance tools.

A user-monitoring process that can also correlate medical text complexity with the health care provider's reading performance, to assess the impact of this interaction between text and reader on other extrinsic measures of health care delivery, such as patient-satisfaction, complication rates, adverse outcomes, patient survival, and other long-term effects of complex medical decision making. A medical text having too high of a level of complexity might lead to one or more medical professionals being unable to understand portions of the text, or misinterpreting portions of the text which can potentially lead to adverse health outcomes for patients. Additionally, a medical text having too low of a level of complexity may not accurately convey all information that is necessary for a medical professional to make an informed decision.

In some implementations, a text enhancement and reading improvement system combines a medical text complexity analyzer with a long-term health care outcomes analyzer that can track long-term and temporally remote, multifactorial interactions of the complexity factors on health care outcomes. For example, linguistically complex medical texts may predict better outcomes for patients, provided that the physician-readers of those texts are able to comprehend them effectively and efficiently, using the text display enhancing supports described above, if necessary. The system could therefore identify optimal conditions for health care delivery that determine the most appropriate level of text complexity (e.g., not too simple, as that could worsen outcomes, but not too complex, as the reading time may be too long, or too easily misinterpreted, and not adding real additional value to health outcomes anyway). Information on the correlations between text complexity levels, health care provider's reading performance, and healthcare outcomes can be used to improve patient outcomes by identifying optimum medical text complexity levels for different readers. This can allow text complexity of existing texts to be modified to achieve an optimum complexity level, while allowing for texts created in the future to be created at or near an optimum complexity level. The system could additionally, after determining optimal text complexity for health outcomes, focus and refine the operations of reading support tools that various health care providers can utilize to read the text effectively and efficiently.

For some medical conditions, a team of health care providers may be weighing the risks and benefits, (worst case scenario/best case scenario), relative probabilities of certain outcomes (e.g., sensitivity and specificity of test results, success rates and complication rates of surgery, etc.). In some circumstances, longer sentences, each with relative clauses that qualify or juxtapose certain conditions relative to others, may be most effective in getting the health care team to agree on and implement a complex plan of care—and this effectiveness can be tracked with the ultimate health care outcomes associated with that part of the medical record. However, in other conditions, or, for example, when there are different kinds of members of the health care team having different levels of experience or expertise, long and complex sentences can carry a risk of being too long and too complex, and the group's (or a key individual's) understanding of why and how to implement a plan may be compromised. In such conditions, a sentence-complexity analyzer could warn the author that the sentence needs to be simplified. This determination that the sentence is too long can be based on characteristics associated with the intended reader or readers, or the subject matter of the text, or both.

In some implementations, a text analysis and enhancement system can be employed not only to enhance the display of text for improved readability, but also to provide direct data on the medical text itself, with new measures of linguistic complexity that are currently not available in standard readability software. For example, the text-analysis steps can determine whether certain medical passages contain linguistic ambiguities that increase the risk of misinterpretation, which, in turn, could have adverse health outcomes, across a wide range of readers at any level of proficiency. The process can be used to highlight or alert readers where in the text such ambiguities are, without changing the words or text itself, so that readers can pay more attention to identified segments of the text and be sure to interpret these identified segments with extra care.

The features described in this disclosure can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing context.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A computer-implemented method for enhancing text presentation from a machine readable natural language text to improve reading comprehension, the method comprising:
retrieving, by one or more computer systems, a machine readable natural language text from one or more computer readable memory storage locations;
determining, by the one or more computer systems, a domain for the machine readable natural language text;
accessing, by the one or more computer systems, an electronic database of domain-specific multiple-word phrases that is specific to the determined domain for the machine readable natural language text, where the electronic database includes indications of parts of speech for the domain-specific multiple-word phrases;
parsing, by the one or more computer systems, the machine readable natural language text to identify text specific attributes of the machine readable natural language text, including identifying one or more domain-specific multiple-word phrases by comparing the machine readable natural language text to information included in the electronic database;
identifying, by the one or more computer systems, parts-of-speech for one or more of the identified domain-specific multiple-word phrases within the machine readable natural language text;
based on identifying the parts-of-speech for the one or more of the identified domain-specific multiple-word phrases within the machine readable natural language text, inserting, for each of the one or more of the identified domain-specific multiple-word phrases, a computer readable tag identifying the identified part-of-speech for the identified domain-specific multiple-word phrase within the machine readable natural language text;
storing, by the one or more computer systems and on one or more computer readable memory devices, the machine readable natural language text along with the computer readable tags; and
varying, by the one or more computer systems, a presentation of the text based at least in part on the computer readable tags identifying the identified part-of-speech for each of the one or more identified domain-specific multiple-word phrases within the machine readable natural language text.

2. The method of claim 1, wherein:
the determined domain for the machine readable natural language text is a medical text domain;
the electronic database of domain-specific multiple-word phrases is an electronic database of medical-specific multiple-word phrases;
the machine readable natural language text comprises an electronic medical text; and
varying the presentation of the machine readable natural language text includes varying the presentation of the electronic medical text for human reading.

3. The method of claim 2, wherein the electronic database is derived from medical texts accessible in multi-record electronic medical record systems.

4. The method of claim 1, wherein identifying one or more domain-specific multiple-word phrases includes:
identifying a first set of domain-specific multiple-word phrases in the text;
determining, for each domain-specific multiple-word phrase in the first set of domain-specific multiple-word phrases, if the particular domain-specific multiple-word phrase should be treated as a single term or if each individual word in the particular domain-specific multiple-word phrase should be treated as an individual term; and
identifying a second set of domain-specific multiple-word phrases from the first set of domain-specific multiple-word phrases that includes only domain-specific multiple-word phrases that have been determined to be treated as single terms.

5. The method of claim 1, wherein the part-of-speech identified for each of the one or more domain-specific, multiple-word phrase is determined based at least in part on a part-of-speech of a word preceding or following the domain-specific, multiple-word phrase within a sentence that includes the domain-specific, multiple-word phrase.

6. The method of claim 1, wherein parsing the text to identify text specific attributes of the text includes use of proximate word-to-word, rule-based, sentence-specific context extractors to disambiguate words or domain-specific multiple-word phrases with multiple possible parts-of-speech into a particular, context-specific part-of-speech.

7. The method of claim 1, wherein parsing the machine readable natural language text to identify text specific attributes of the text includes performing clause-pattern recognition to incrementally and recursively extract and label clauses that are embedded within other phrases and clauses in the machine readable natural language text, wherein labeling the extracted clauses includes inserting clause-encapsulating tags into the machine readable machine readable natural language text, each of the clause-encapsulating tags comprising one or more computer readable tags associated with a particular location within the machine-readable natural language text.

8. The method of claim 1, wherein varying the presentation of the text includes varying the spatial presentation of the text without removing, changing, or adding new words to original words of the text, and without changing the linear sequence (left to right, top to bottom) of original characters of the text.

9. The method of claim 1, wherein parsing the text to identify text specific attributes of the text includes identifying a difficulty level, frequency of use, and length of one or more words used in the text.

10. The method of claim 1, wherein varying the presentation of the text includes varying spatial presentation of the text by using the computer readable tags identifying the identified part-of-speech for the one or more identified domain-specific multiple-word phrases to segment sentences into shorter segments that are placed on separate rows.

11. The method of claim 1, wherein varying the presentation of the text includes using the computer readable tags identifying the identified part-of-speech for each of the one or more identified domain-specific multiple-word phrases within the text to vary the presentation of the text by assigning varying colors to the multi-word, domain-specific, part-of-speech.

12. The method of claim 1, wherein varying the presentation of the text includes gauging the presentation of the text based on an identified attribute of a reader of the text.

13. The method of claim 1, further comprising:
identifying a linguistic ambiguity within the text; and
displaying an indication of the linguistic ambiguity.

14. The method of claim 1, further comprising:
determining that a particular one of the identified domain-specific multiple-word phrases should not be identified as a multi-word phrase based on an identification of a part of speech of a word preceding or following the particular one of the identified domain-specific multiple-word phrases within a sentence that includes the particular one of the identified domain-specific multiple-word phrases.

15. The method of claim 1, wherein identifying parts-of-speech for one or more of the identified domain-specific multiple-word phrases within the machine readable natural language text includes examining an immediately adjacent word or domain-specific multiple-word phrase for disambiguation, conjugation and coordination.

16. The method of claim 1, further comprising:
for each identified domain-specific multiple-word phrase, inserting a pair-binding tag between the words of the domain-specific multiple-word phrase, wherein the pair-binding tag comprises a computer readable tag associated with a particular location within the machine-readable natural language text.

17. The method of claim 16, wherein the pair-binding tag inserted between the words of each identified domain-specific multiple-word phrase has a pair-binding tag type that is dependent on a set of syntactic attributes for each word in the domain-specific multiple-word phrase.

18. One or more non-transitory computer readable storage mediums encoded with instructions that, when executed by one or more processors, cause the one or more processors to perform actions comprising:
retrieving, by one or more computer systems, a machine readable natural language text from one or more computer readable memory storage locations;
determining, by the one or more computer systems, a domain for the machine readable natural language text;
accessing, by the one or more computer systems, an electronic database of domain-specific multiple-word phrases that is specific to the determined domain for the machine readable natural language text, where the electronic database includes indications of parts of speech for the domain-specific multiple-word phrases;
parsing, by the one or more computer systems, the machine readable natural language text to identify text specific attributes of the machine readable natural language text, including identifying one or more domain-specific multiple-word phrases by comparing the machine readable natural language text to information included in the electronic database;
identifying, by the one or more computer systems, parts-of-speech for each one or more of the identified domain-specific multiple-word phrases within the machine readable natural language text;
based on identifying the parts-of-speech for the one or more of the identified domain-specific multiple-word phrases within the machine readable natural language text, inserting, for each of the one or more of the identified domain-specific multiple-word phrases, a computer readable tag identifying the identified part-of-speech for the identified domain-specific multiple-word phrase within the machine readable natural language text;
storing, by the one or more computer systems and on one or more computer readable memory devices, the machine readable natural language text along with the computer readable tags; and
varying, by the one or more computer systems, a presentation of the text based at least in part on the computer readable tags identifying the identified part-of-speech for each of the one or more identified domain-specific multiple-word phrases within the machine readable natural language text.

19. The one or more non-transitory computer readable storage mediums of claim 18, wherein varying the presentation of the text includes varying spatial presentation of the text by using the computer readable tags identifying the identified part-of-speech for the one or more identified domain-specific multiple-word phrases to segment sentences into shorter segments that are placed on separate rows.

20. The one or more non-transitory computer readable storage mediums of claim 18, the actions further comprising:
determining that a particular one of the identified domain-specific multiple-word phrases should not be identified as a multi-word phrase based on an identification of a part of speech of a word preceding or following the particular one of the identified domain-specific multiple-word phrases within a sentence that includes the particular one of the identified domain-specific multiple-word phrases.

* * * * *